United States Patent [19]

Toda et al.

[11] Patent Number: 4,857,537
[45] Date of Patent: Aug. 15, 1989

[54] NOVEL THIAZOLIDINE DERIVATIVES

[75] Inventors: Masaaki Toda, Osaka; Shuichi Ohuchida, Kyoto; Hiroyuki Ohno, Shiga, all of Japan

[73] Assignee: Ono Pharmaceutical Co., Ltd., Japan

[21] Appl. No.: 159,073

[22] Filed: Feb. 23, 1988

[30] Foreign Application Priority Data

Feb. 23, 1987 [JP] Japan ................................... 62-37844

[51] Int. Cl.$^4$ .................... C07D 277/04; B61K 31/425
[52] U.S. Cl. ...................................... 514/365; 514/311; 514/342; 546/105; 546/209; 548/200; 548/201
[58] Field of Search ......................................... 548/200

[56] References Cited

U.S. PATENT DOCUMENTS 4,701,465  10/1987  Tanaka ................................ 514/423

FOREIGN PATENT DOCUMENTS 0154353  9/1985  European Pat. Off. .
0172458  2/1986  European Pat. Off. .
0201741  11/1986  European Pat. Off. .
0201742  11/1986  European Pat. Off. .
0201743  11/1986  European Pat. Off. .

OTHER PUBLICATIONS

Chemical Abstracts, vol. 98, No. 9, Feb. 28, 1983, p. 638, abstract 72145x.

Primary Examiner—Robert Gerstl
Attorney, Agent, or Firm—Sughrue, Mion, Zinn, Macpeak & Seas

[57] ABSTRACT

A novel thiazolidine derivative of general formula:

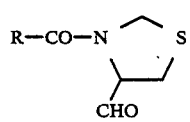

(I)

[wherein R represents a group of general formula:

G-E-D-B-A-

(wherein A represents single bond, alkylene group of from 1 to 6 carbon atom(s), alkylene group of from 2 to 6 carbon atoms, a group of general formula:

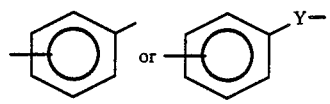

or saturated hydrocarbon ring of from 4 to 7 carbon atoms or single heterocyclic ring.

Y represents alkylene group of from 1 to 4 carbon atom(s) or alkenylene group of from 2 to 4 carbon atoms.

B represents single bond or alkylene group of from 1 to 6 carbon atom(s).

D represents single bond, oxygen atom, carbonyl group or a group of general formula:

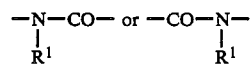

$R^1$ represents hydrogen atom, alkyl group of from 1 to 4 carbon atom(s), phenyl group or benzyl group.

E represents single bond, alkylene group of from 1 to 8 carbon atom(s) or alkylene group of from 1 to 8 carbon atom(s) substituted by phenyl group or benzyl group.

G represents carbocyclic or heterocyclic ring unsubstituted or substituted by from one to three of alkyl group of from 1 to 6 carbon atom(s), alkoxy group of from 1 to 6 carbon atom(s), halogen atom, trifluoromethyl group or nitro group.)

With the proviso that, A and B do not represent mono-bonds at the same time.]

possess inhibitory activity on prolyl endopeptidase, and therefore be useful for treating and/or preventing agent for amnesia.

18 Claims, No Drawings

NOVEL THIAZOLIDINE DERIVATIVES

SUMMARY

This invention is related to novel compounds having an inhibitory activity on prolyl endopeptidase.

More particularly, this invention, is related to (1) Novel thiazolidine derivatives having an inhibitory activity on prolyl endopeptidase, of the following general formula:

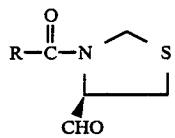
(I)

[wherein all of the symbols are the same meaning as hereafter defined.]

(2) process for the preparation of them, and (3) anti-amnesia agent containing them as active ingredient.

BACKGROUND

Recent advance in neuroscience is making clear the natural shape of neurotransmitter, substance deeply related to memory in brain. It is said that some of these substances are neuropeptides containing prolines.

Recovery of the memory was reported by the dose of neuropeptide containing proline to experimental amnesia rat (See Science 211, 601 (1981)).

On the other hand, it is presumed that these neuropeptide-hormons shall be matabolized by cerebral endogenous peptidases. Especially, prolyl endopeptidase (EC, 3. 4. 21. 26) might take part in these metabolism closely (See J. Biochem., 94, 1179 (1983)).

From these facts, the studies were in progress that it should be possible to prevent or treat amnesia by inhibiting prolyl endopeptidase and suppressing the metabolism of neutrotransmitter. (See Protein, Nucleic acid and Enzyme 25(6), 513(1980); Nippon Nougei Kagaku Kaishi 58(11), 1147(1984); J. Neurochem., 41, 69(1983); ibid 42, 237(1984).)

For the purpose described above, several compounds were synthesized. For example, it is clear that N-benzyloxycarbonyl-glycyl-L-prolyl-chloromethane, N-benzyloxycarbonyl-L-prolyl-prolinal strongly inhibit prolyl endopeptidase (See J. Neurochem., 41, 69(1983)). More recently, it is disclosed that compounds shown below are effective for the above purpose.

(i) Prolinal derivatives of general formula

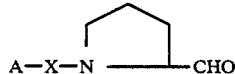
(A)

[wherein A represents a protecting group of amino acid group in the field of amino acid chemical, and X represents a residual group of amino acid.]

See Japanese Patent Kokai No. 60-188317, i.e. European Patent Publication No. 154353.

(ii) N-acylpyrrolidine derivatives of general formula

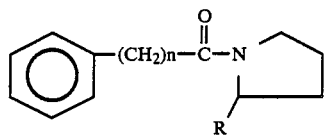
(B)

[wherein n represents a number of 1~4, and R represents lower alkyl ester group, —$CH_2OH$ group or aldehyde group.]See Japanese Patent Kokai No. 61-37764; a compound wherein n is 5 is also disclosed by correction, i.e. European Patent Publication No. 172458.

(iii) Compounds of general formula

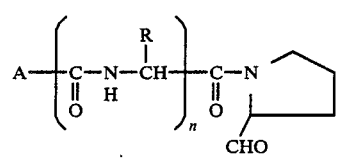
(C)

[wherein A represents methyl group or benzyloxy group, R represents isopropyl group or isobutyl group on condition that plural R's are same meaning in one formula. And n represents 2 or 3.]

See Japanese Patent Kokai No. 61-183297.

Most recently, five applications related to anti-amnesia agents having prolinal skeltons were published. i.e.

(iv) Compounds of general formula

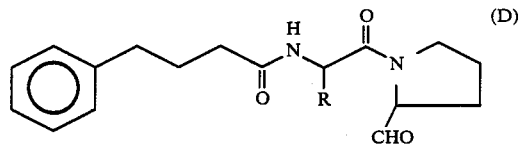
(D)

[wherein R represents a group of

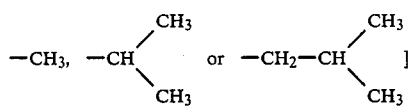

]

See Japanese Patent Kokai No. 61-238775, i.e. European Patent Publication No. 201741.

(v) N-acylpyrrolidine derivatives of general formula

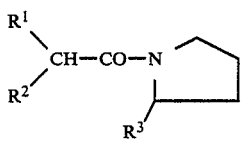
(E)

[wherein $R^3$ represents lower alkyloxycarbonyl group, hydroxymethyl group or formyl group, $R^1$ represents a hydrogen atom or lower alkyl group, $R^2$ represents phenyl group or a group of the following general formula:

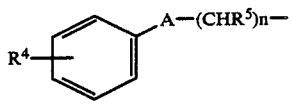

(wherein R[4] represents a hydrogen atom, a halogen atom or lower alkoxy group, R[5] represents a hydrogen atom or lower alkyl group, n represents 0 or 1, A represents an oxygen atom, methylene group, hydroxymethylene group, phenylmethylene group or carbonyl group.) or R[1] and R[2] represent, together with, benzylidene group unsubstituted or substituted by aromatic ring(s).]

See Japanese Patent Kokai No. 61-238776, i.e. European Patent Publication No. 201742.

(vi) Compounds of general formula

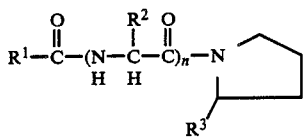

[wherein n represents a number of 0~2. R[1] represents a straight-chained organic group of from 5 to 25 carbon atoms which is saturated or unsaturated. Wherein, unsaturated carbon chain may be contained plural number of double bonds. R[2] represents a group of

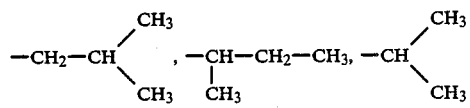

R[3] represents lower alkyl ester group, —CH$_2$OH group or aldelyde group.]

See Japanese Patent Kokai No. 61-238799, i.e. European Patent Publication No. 201743.

(vii) Compounds of general formula

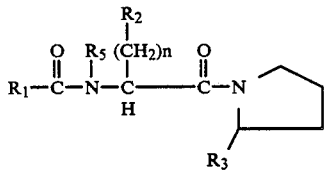

[wherein n is an integer of more than one, R$_1$ is a saturated or unsaturated straight-chained hydrocarbon group of from 5 to 25 carbon atoms. Herein said, unsaturated carbon chain may be contained plural number of double bonds. R[3] represents lower alkyl ester group of the formula: —COOR[4] (wherein R[4] represents lower alkyl group.), hydroxymethyl group or formyl group, R[2] represents methyl group, phenyl group, hydroxyphenyl group, indolyl group, imidazolyl group, carboxyl group, formyl group, amino group, hydrowy group, hydroxyalkyl group, thiol group, methylthio group or guanidino group etc. and each of above group may be substituted. R[5] represents a hydrogen atom or a single bond between carbon atom and nitrogen atom together with R[2] when n is 3.]

See Japanese Patent Kokai No. 62-84058, i.e. European Patent Publication No. 201743.

(viii) Dipeptide derivatives of general formula

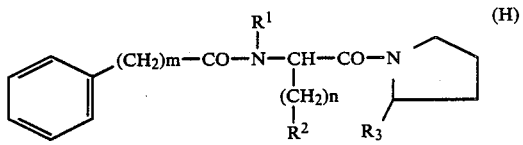

[wherein m represents an integer of 1~8, n represents an integer of 1~6, R[1] represents a hydrogen atom, R[2] represents a hydrogen atom, a branched alkyl group of from 3 to 5 carbon atoms, phenyl group, hydroxyphenyl group, indolyl group, imidazolyl group or methylthio group, or a single bond between carbon atom and nitrogen atom together with R[1]. R[3] represents lower alkyl ester group, hydroxymethy group or formyl group.]

See Japanese Patent Kokai No. 62-148467, i.e. European Patent Publication No. 201741.

And more the present inventors have been filed an application related to prolinal derivatives having an activity of anti-amnesia, in advance of the present application, i.e.

(ix) Prolinal derivatives of general formula

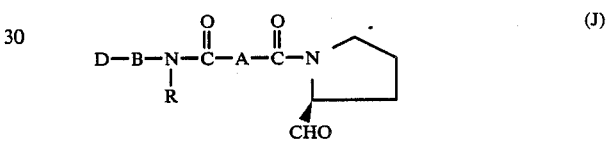

[wherein A represents alkylene or alkenylene group of from 1 to 8 carbon atom(s) or a saturated hydrocarbon ring of from 3 to 7 carbon atoms, R represents hydrogen atom, phenyl group, benzyl group, alkyl group of from 1 to 8 carbon atom(s) or cycloalkyl group of from 3 to 7 carbon atoms, B represents alkylene group of from 1 to 8 atom(s) unsubstituted or substituted by phenyl group or benzyl group or a single bond, D represents carbocyclic or heterocyclic ring unsubstituted or substituted by from one to three of halogen atom, alkyl or alkoxy group of from 1 to 4 carbon atom(s), nitro group or trifluoromethyl group.]

See European Patent Application No. 87116613.8.

Comparison with the Prior Arts

The compounds of the present invention of the general formula (I) are different from the compounds of the general formula (A)~(H) and compounds in the literature (J. Neurochem., 41) in structure. The compounds of the present invention are novel compounds which have necessarily thiazoline ring as basic skelton.

And, we the present inventors have have confirmed in the previous application (compounds represented by the general formula (J)) that compounds wherein benzene ring was replaced by other aromatic rings (including heterocyclic rings and saturated rings, e.g. naphthalene, fluorene, furan rings) have also been maintained the inhibitory activity on prolyl endopeptidase in the results of several modification in D.

Among the compounds of the present invention which are the compounds modified the compounds of the general formula (J) in the parts other than D, it is not difficult to forecast that the compounds wherein D was replaced by the other rings should have maintained the activity, if the compounds wherein D is benzene ring have enough activity.

Disclosure of the Invention

The present invention is related to (1) A novel thiazolidine derivative of general formula:

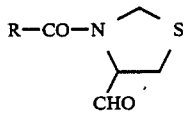 (I)

8 wherein R represents a group of general formula:

G-E-D-B-A-

(wherein A represents single bond, alkylene group of from 1 to 6 carbon atom(s), alkenylene group of from 2 to 6 carbon atoms, a group of general formula:

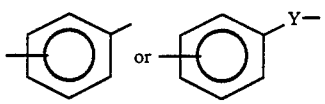

or saturated hydrocarbon ring of from 4 to 7 carbon atoms or mono heterocyclic ring.

Y represents alkylene group of from 1 to 4 carbon atom(s) or alkenylene group of from 2 to 4 carbon atoms.

B represents single bond or alkylene group of from 1 to 6 carbon atom(s).

D represents single bond, oxygen atom, carbonyl group or a group of general formula:

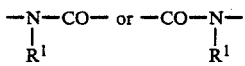

$R^1$ represents hydrogen atom, alkyl group of from 1 to 4 carbon atom(s), phenyl group or benzyl group.

E represents single bond, alkylene group of from 1 to 8 carbon atom(s) or alkylene group of from 1 to 8 carbon atom(s) substituted by phenyl group or benzyl group.

G represents carbocyclic or heterocyclic ring unsubstituted or substituted by from one to three of alkyl group of from 1 to 6 carbon atom(s), alkoxy group of from 1 to 6 carbon atom(s), halogen atom, trifluoromethyl group or nitro group.)

With the proviso that, A and B do not represent single bonds at the same time.]

(2) Process for the preparation of them and (3) Anti-amnesia agent containing them as active ingredient.

In the general formula (I), "alkylene group of from 1 to 6 carbon atom(s)" represented by A or B means methylene, ethylene, trimethylene, tetramethylene, pentamethylene and hexamethylene groups and isomeric groups thereof.

In the general formula (I), "alkylene group of from 1 to 8 carbon atom(s)" represented by E means groups described above including heptamethylene and octamethylene groups and isomeric group thereof.

In the general formula (I), "alkylene group of from 1 to 4 carbon atom(s)" represented by Y means methylene, ethylene, trimethylene and tetramethylene groups and isomeric groups thereof.

In the general formula (I), "alkenylene group of from 2 to 4 carbon atoms" represented by Y means vinylene, propenylene, butenylene and butadienylene groups and isomeric groups thereof.

In the general formula (I), "alkenylene group of from 2 to 6 carbon atoms" represented by A means groups described above including pentenylene, pentadienylene, hexenylene, hexadienylene and hexatrienylene groups and isomeric groups thereof.

In the general formula (I), "saturated hydrocarbon ring of from 4 to 7 carbon atoms" represented by A means cyclobutane, cyclopentane, cyclohexane and cycloheptane rings.

In the general formula (I), "mono-heterocyclic ring" represented by A means aromatic heterocyclic rings containing 4 to 7 ring members including 1 or 2 hereto atom(s), which may be partially or fully saturated.

Examples of the rings mentioned above are furan, thiophene, pyrrole, oxazole, isoxazole, thiazole, isothiazole, imidazole, pyrazole, furazane, pyran, pyridine, pyridazine, pyrimidine, pyrazine rings and partially or fully saturated rings thereof.

In the general formula (I), preferred mono-heterocyclic rings represented by A especially are piperidine, pyrrolidine and thiazolidine rings.

In the general formula (I), "alkyl group of from 1 to 4 carbon atom(s)" represented by $R^1$ means methyl, ethyl, propyl and butyl groups and isomeric groups thereof.

In the general formula (I), "carbocyclic ring" represented by G means mono-, bi- or tri-cyclic aromatic carbocyclic ring(s) containing not more than 15 carbon atoms which may be partially or fully saturated.

Examples of the rings mentioned above are benzene, naphthalene, indene, azulene, fluorene, phenanthrene, anthracene, acenaphthalene, biphenylene rings and partially or fully saturated rings thereof.

In the general formula (I), "heterocyclic ring" represented by G means mono-, bi- or tri-aromatic heterocyclic ring(s) containing not more than 15 carbon and hetero atoms which may be partially or fully saturated. In above heterocyclic rings, rings containing one or two of hetero atom(s) are preferred.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinoxaline, phthalazine, pteridine, carbazole, acridine, phenanthridine, xanthene, phenazine, phenothiazine rings and partially or fully saturated rings thereof.

In the general formula (I), preferred rings represented by G especially are benzene, naphthalene, fluorene, pyridine, furan, isoquinoline and acridine rings and partially saturated rings thereof.

In the above rings, substituted benzene rings are preferred as substituted rings by substituent(s).

In the general formula (I), "alkyl group of from 1 to 6 carbon atom(s)" in G means groups described above including pentyl and hexyl groups and isomeric groups thereof, and "alkoxy group of from 1 to 6 carbon atom(s)" in G means methoxy, ethoxy, propoxy, butoxy, pentyloxy and hexyloxy groups and isomeric groups thereof.

In the general formula (I), "halogen atom" in G means chlorine, bromine, fluorine and iodine atoms.

Throughout the specification including claims, stereo isomers generated by stereo configuration(s) (asymmetric carbon, double bond etc.) and structural isomers generated by branch of carbon chain etc. are included in the present invention.

For example, it may be easily understood that alkylene and alkenylene groups include straight-chained and also branched-chained ones, to the skilled in the art.

Rings represented by A or rings in G may be attached to the adjoining group with any position.

Process for the Preparation

According to the present invention, the compounds of the present invention of the general formula (I) may be prepared by oxidizing a compound of general formula:

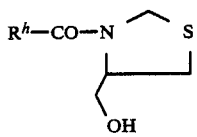
(II)

[wherein $R^h$ represents a group of general formula:

$$G-E-D^h-B-A-$$

(wherein $D^h$ represents single bond, oxygen atom, oxo carbonyl group or a group of general formula:

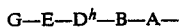

(wherein all of the symbols are the same meaning as defined hereinbefore.) or hydroxymethylene group.

And the other symbols are the same meaning as defined hereinbefore.] in a mild condition.

Oxidation in a mild condition is known and may be carried out, for example, using an oxidation agent (sulfur trioxide—pyridine complex, chromium trioxide—pyridine complex, t-butyl chloroformate, oxalyl chloride etc.), with a tertiary amine (triethylamine, pyridine etc.) or without, in an inert organic solvent (DMSO, methylene chloride, chloroform, benzene etc.), at a temperature of from 0° C. to 50° C.

Alcohols of the general formula (II) may be prepared by reducing a carboxylic acid or their ester of general formula:

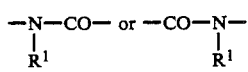
(III)

[wherein R' represents hydrogen atom or alkyl group of from 1 to 6 carbon atom(s), and the other symbols are the same meaning as defined hereinbefore.]

Reduction is known and may be carried out, for example, using a reducing agent (lithium borohydride etc.), in an organic solvent (THF, methanol, ethanol, etc.), at a temperature of from −40° C. to 20° C.

Carboxylic acid and their ester of the general formula (III) may be prepared by reacting thiazolidine of general formula:

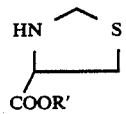
(IV)

and a carboxylic acid of general formula:

$$R-COOH \quad (V)$$

[wherein all of the symbols are the same meaning as hereinbefore defined.] to form an amide bond.

Reaction to form amide bond with a carboxylic acid and a secondary amine is knowna, and it may be carried out, for example, by (1) mixed acid anhydride method, e.g. using an acid halide (pivaloyl chloride etc.) or an acid derivative (ethyl chloroformate, isobutyl chloroformate etc.), in the presence of a tertiary amine (triethylamine etc.), in an inert organic solvent (THF, methylene chloride, chloroform, ethyl ether etc.), at a temperature of from 0° C. to 50° C.), (2) acid halide method, e.g. reacting acid halide (oxalyl chloride etc.) and a compound of general formula (V) in an inert organic solvent (same as described above.), and the resulting acid halide is reacted with an amine of the general formula (IV), in the presence of tertiary amine (triethylamine, pyridine, N-methylmorpholine etc.) at a temperature of from 0° C. to 50° C., (3) using an activating agent such as DCC, e.g. using an activating agent (DCC, diisopropylcarbodiimide, 1-[3-(N,N-diethylamino)propyl]-3-ethylcarbodiimide etc.), with a tertiary amine or without, with another activating agent (1-hydroxybenzotriazole etc.) or without, in an inert organic solvent (THF, methylene chloride, chloroform, ethyl ether etc.), at a temperature of from 0° C. to 50° C.

The compounds of the general formula (IV) and (V) are known per se or may be prepared by known method.

Throughout the specification, in each reactions, products may be purified by conventional methods, for example, distillation at atmospheric or reduced pressure, high performance liquid chromatography, thin layer chromatography using silica gel or magnesium silicate or washing or recrystallization. Purification may be carried out after each reactions or a series of reactions.

Pharmacological Activities

The compounds of the present invention of the general formula (I) possess an inhibitory activity on prolyl endopeptidase, described before, for example, in a standard laboratory test, results in the followings are given.

Prolyl endopeptidase inhibitory activity in vitro

The compounds of the present invention showed activites as in the following Table I, with the test system described hereafer.

TABLE I

| Example No. of the compounds | Concentration for 50% inhibition IC$_{50}$ (μM) |
|---|---|
| 1 (b) | 0.73 |
| 1 (c) | 0.087 |
| 1 (g) | 4.8 |

TABLE I-continued

| Example No. of the compounds | Concentration for 50% inhibition IC$_{50}$ (μM) |
| --- | --- |
| 1 (i) | 8.1 |
| 1 (k) | 0.016 |
| 1 (l) | 0.022 |
| 1 (n) | 0.02 |
| 1 (q) | 0.0057 |
| 1 (s) | 0.0068 |
| 1 (t) | 0.035 |
| 1 (v) | 0.083 |

Inhibitory activity of prolyl endopeptidase in vitro was measured by the following test system.

A mixed solution of 20 mM tris-HCl buffer (pH 7.5; 935 μl; containing 10 mM EDTA and 10 mM mercaptoethanol), a solution of a compound of the present invention in DMSO (10 μl) and a solution of prolyl endopeptidase which was purified from bovine brain (0.13 unit; prepared by the method described in J. Biochem., 94, 1179 (1983)) in tris-HCl buffer (15 μl) was preincubated for 15 mins at 37° C.

To the solution, 5 mM of N-benzyloxycarbonyl-glycyl-prolyl-p-nitroanilide (40 μl) in a mixture of 40% dioxane—60% water was added. Ths solution was incubated for 1 min at the same temperature.

Optical absorption (a$_1$) at 405 nm of the solution, and optical absorption (a$_2$) at 405 nm of the solution after more 30 mins' incubation at 37° C. were measured.

Optical absorptions (b$_1$ and b$_2$) of the solutions using DMSO instead of the solution of the compound of the present invention were also measured.

Inhibitory ratio was calculated by the following expression and IC$_{50}$ (required concentration for 50% inhibition) was obtained (See Protein, Nucleic acid and Enzyme 25(6), 513, 1980.).

$$\text{Inhibitory ratio (\%)} = \frac{(b_2 - b_1) - (a_2 - a_1)}{b_2 - b_1} \times 100$$

Toxicity

On the other hand, it was confirmed that the toxicity of the compounds of the present invention were very low. Therefore, the compounds of the present invention may be considered to be sufficiently safe and suitable for pharmaceutical used.

Application for the Pharmaceuticals

To inhibit prolyl endopeptidase is to suppress the metabolism of neurotransmitter, substances taking part in memory in brain (each of them is peptide.) described hereinbefore, and therefore be useful for prevention and/or treatment for amnesia, in animals including human beings, especially human beings.

The compounds of the present invention possess a inhibitory activity on prolyl endopeptidase in vitro, so it is expected to be useful for prevention and/or treatment of amnesia.

For the purposes above described, the compounds of the present invention may normally be administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 500 mg, by oral administration, up to several times per day, and between 1 mg and 100 mg, by parenteral administration (preferably, intravenous administration) up to several times per day.

As mentioned above, the doses to be used depend upon various conditions. Therefore, there are cases in which does lower than or greater than the ranges specified above may be used.

At the administration, the compounds of the present invention may be formed into solid compositions, liquid compositions or the other compositions for oral administration, injection compositions, external composition, suppositories etc. for parenteral administration.

Solid compositions for oral administration, include compressed tablets, pills, dispersible powders, capsules, and grannules. In such compositions, one or more of the active compound(s) is or are, admixed with at least done inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. lubricating agents (magnesium stearate etc.), disintegrating agents (cellulose calcium gluconate etc.), and assisting agent for dissolving (glutamic acid, aspertic acid etc.) stabilizing agent (lactose etc.).

The tablets or pills may, if desired, be coated with film of gastric or enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agents etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.).

For preparation of such spray compositions, for example, the method described in U.S. Pat. Nos. 2868691 or 3095355 may be used.

Injections for parenteral administration include sterile aqueous or non-aqueous solutions, suspensions and emulsions. In such compositions, one or more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

Reference Examples and Examples

The following reference examples and examples are illustrate the present invention, but not limit the present invention.

The solvents in the parentheses show the developing or eluting solvents and the ratios of the solvents used are by volume in chromatographic separations.

Unless otherwise specified, "IR" were measured by liquid film method.

Reference Example 1

Synthesis of
3-[N-(4-methylbenzyl)carbamoyl]propionic acid ethyl ester

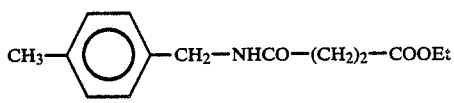

4-methylbenzylamine (0.93 ml) was dissolved into methylene chloride (5 ml), and triethylamine (1.3 ml) was added to the solution. A solution of ethylsuccinyl chloride (0.86 ml) in methylene chloride (2 ml) was added to the solution cooling to 0° C. The temperature of the solution was raised to room temperature gradually with stirring. After stirring for 1.5 hr at room temperature, methylene chloride was added to the solution and the mixture was separated. The oily layer was washed with 1N hydrochloric acid, water, a saturated aqueous solution of sodium bicarbonate and a saturated brine, successively, dried and evaporated. The residue was purified by column chromatography on silica gel (hexane:EtOAc=1:1) to give the title compound (1.59 g) having the following physical data:

TLC:Rf0.43(EtOAc:hexane=1:1).

Reference Example 2

Synthesis of
3-[N-(4-methylbenzyl)carbamoyl]propionic acid

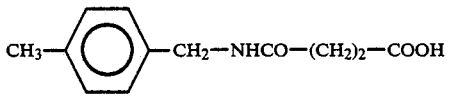

A mixture of alcohol prepared in reference example 1 (1.59 g), ethanol (20 ml) and 2N aqueous solution of sodium hydroxide (13 ml) was stirred for 1 hr. The mixture was evaporated and ethyl acetate was added to the residue. The solution was adjusted to acidic with hydrochloric acid, washed with a saturated brine, dried and evaporated. The residual crystals were washed with a mixed solvent (ethyl acetate:hexane=5:95) to give the title compound (1.12 g) having the following physical data:

TLC:Rf0.09(EtOAc:hexane=8:2).

Reference Example 3

Synthesis of
(4R)-3-[3-[N-(4-methylbenzyl)carbamoyl]propionyl]-thiazilidin-4-carboxylic acid methyl ester

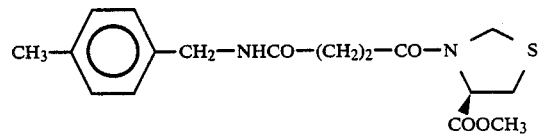

Carboxylic acid prepared in reference example 2 (300 mg) was dissolved into methylene chloride (2 ml). To the solution, triethylamine (2.1 ml) was added to the solution, the solution was cooled to 0° C. Pyvaloyl chloride (0.17 ml) was dropped to the solution and the solution was stirred for 20 mins at the same temperature. A solution of (4R)-thiazilidine-4-carboxylic acid methyl ester hydrochloride (323 mg) in methylene chloride (1.5 ml) and triethylamine (0.5 ml) were dropped to the solution and the solution was stirred for 10 mins at the same temperature and for 1 hr at room temperature. After reaction, hydrochloric acid and ethyl acetate were added to the solution, and the mixture was separated. The oily layer was washed with a saturated aqueous solutin of sodium bicarbonate, a saturated brine, successively, dried and evaporated. The residue was purified by column chromatography on silica gel (ethyl acetate:hexane=8:2) to give the title compound (233 mg) having the following physical data:

TLC: Rf 0.23 (EtOAc:hexane=8:2).

Reference Example 4

Synthesis of
(4R)-3-[3-[N-(4-methylbenzyl)carbamoyl]propionyl]-thiazolidin-4-ol

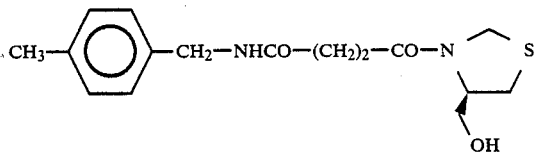

Methyl ester prepared in reference example 3 (233 mg) was dissolved into THF (2.5 ml). A solution of lithium borohydride in THF (2M; 0.67 ml) was dropped into the solution. The solution was stirred for 2 hrs at room temperature. The solution was worked up by adding acetic acid with stirring. The solution was evaporated. To the residue, 1N hydrochloric acid was dropped by portions with stirring. The oily layer separated was washed with water, a saturated aqueous solutions of sodium bicarbonate, a saturated brine, successively, dried and evaporated. The residue was purified by column chromatography on silica gel (ethyl acetate) to give the title compound (97 mg) having the following physical data:

TLC: Rf 0.19 (EtOAc)

Example 1

Synthesis of
(4R)-3-[3-[N-(4-methylbenzyl)carbamoyl]propionyl]-
thiazolidin-4-al

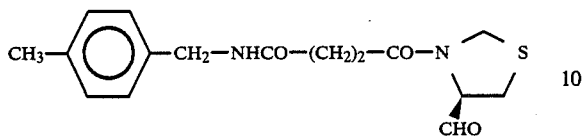

Alcohol prepared in reference example 4 (97 mg) was dissolved into DMSO (2 ml). To the solution, triethylamine (0.25 ml) and a solution of sulfur trioxide-pyridine complex (144 mg) in DMSO (1 ml) secondly. The solution was stirred for 20 mins at room temperature. After reaction, the reaction solution was poured into ice-water. To the mixture, ethyl acetate was added. The oily layer separated was washed with hydrochloric acid, saturated brine, successivly, dried and evaporated. The residue was purified by column chromatography on silica gel (ethyl acetate) to give the title compound (41 mg) having the following physical data:

TLC: Rf 0.50 (EtOAc);

IR: $\nu$ 1720, 1650–1600, 1530–1500, 1410, 790, 740 cm$^{-1}$.

Example 1(a)–1(mm)

By the same procedure as reference example 3, 4 and example 1, each compounds having the following physical data shown in the Table II and III.

With the proviso that, compounds of examples Nos. 1(f), 1(g), 1(k), 1(l), 1(o), 1(q), 1(v), 1(w) and 1(y) were prepared by DCC method, instead of the procedure shown in reference example 3.

In the step described in reference example 4 (reduction), oxo group corresponding to example Nos. 1(j), 1(k), 1(l), 1(m), 1(y), 1(ll) and 1(mm) in R are converted to hydroxy group (R$^h$).

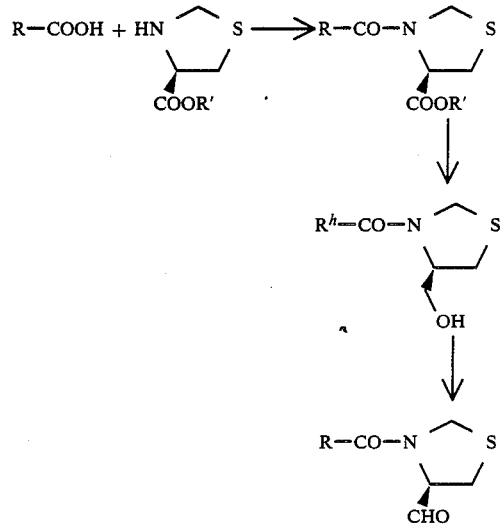

TABLE II

| No. | R— | Name | TLC (Rf) | IR ($\nu$cm$^{-1}$) |
|---|---|---|---|---|
| 1 (a) | φ-(CH$_2$)$_3$— | (4R)—3-(4-phenylbutyryl)thiazolidin-4-al | 0.37 (hexane: EtOAc = 1:1) | 1720, 1630, 1400, 750, 690 |
| 1 (b) | φ-(CH$_2$)$_9$— | (4R)—3-(10-phenyldecanoyl)thiazolidin-4-al | 0.48 EtOAc = 1:1 | 1720, 1630, 1390, 740, 685 |
| 1 (c) | φ-(CH$_2$)$_5$–CH(iPr)– | (4R)—3-(2-isopropyl-7-phenyl heptanoyl)thiazolidin-7-al | 0.45 (hexane: EtOAc = 1:1) | 1720, 1630, 1400, 740, 690 |
| 1 (d) | φ-(CH$_2$)$_3$–cyclohexyl– | (4R)—3-[2-(4-phenylbutyl) cyclohexanecarbonyl]thiazolidin-4-al | 0.42 (hexane: EtOAc = 1:1) | 2900, 2840, 1720, 1620, 1480, 1430, 1400, 740, 690 |
| 1 (e) | Cl-φ-(CH$_2$)$_5$–CH(iPr)– | (4R)—3-[7-(4-chlorophenyl)-2-isopropylheptanoyl]thiazolidin-4-al | 0.36 (hexane: EtOAc = 1:1) | 1725, 1630, 1480, 1400, 1240, 1080 |
| 1 (f) | CH$_3$–(CH$_2$)$_3$–φ–(CH$_2$)$_2$— | (4R)—3-[3-(4-butylphenyl)propionyl]thiazolidin-4-al | 0.27 (hexane: EtOAc = 1:1) | 2910, 2840, 1720, 1640, 1400 |

TABLE II-continued

| No. | R— | Name | TLC (Rf) | IR (νcm⁻¹) |
|---|---|---|---|---|
| 1 (g) | 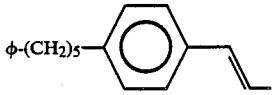 φ-(CH₂)₅— | (4R)—3-[4-(5-phenylpentyl) cinnamoyl]thiazolidin-4-al | 0.33 (hexane: EtOAc = 1:1) | 2910, 1730, 1640, 1600, 1385, 750, 690 |
| 1 (h) | 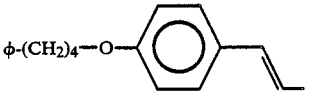 φ-(CH₂)₄—O— | (4R)—3-[4-(4-phenylbutoxy) cinnamoyl]thiazolidin-4-al | 0.28 (hexane: EtOAc = 1:1) | 2930, 1720, 1640, 1590, 1510, 1420, 1390, 1300, 1245, 1170, 820, 750, 690 |
| 1 (i) | φ-CH₂—O—(CH₂)₃— | (4R)—3-(4-benzyloxybutyryl) thiazolidin-4-al | 0.43 (hexane: EtOAc = 1:2) | 1720, 1630, 1400, 1260, 1090, 730, 690 |
| 1 (j) | φ-CO—(CH₂)₂— | (4R)—3-(4-oxo-4-phenylbutyryl) thiazolidin-4-al | 0.57 (EtOAc) | 1720, 1640~1610, 1400, 740, 680 |
| 1 (k) | φ-(CH₂)₃—CO—(CH₂)₂— | (4R)—3-(4-oxo-7-phenylheptanoyl) thiazolidin-4-al | 0.50 (EtOAc) | 1725, 1710, 1640, 1400 |
| 1 (l) |  φ-(CH₂)₂—CO  | (4R)—3-[(2R)—2-(3-phenylpropionyl) cyclopentanecarbonyl]thiazolidin-4-al | 0.42 (hexane: EtOAc = 1:1) | 1720, 1690, 1625, 1400, 735, 690 |
| 1 (m) | 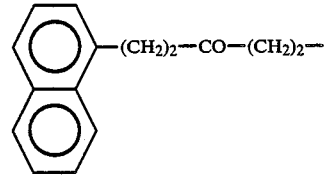 —(CH₂)₂—CO—(CH₂)₂— | (4R)—3-[6-(1-naphthyl)-4-oxohexanoyl]thiazolidin-4-al | 0.31 (EtOAc: hexane = 2:1) | 1725, 1715, 1640, 1405, 1370, 1240, 1095, 1040, 800, 780 |
| 1 (n) | 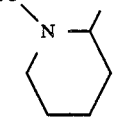 φ-(CH₂)₂—CO  | (4R)—3-[1-(3-phenylpropionyl) piperidine-2-carbonyl]thiazolidin-4-al | 0.47 (EtOAc: hexane = 2:1) | 1720, 1620, 1390, 1240, 1150, 1000, 740, 690 |
| 1 (o) |  φ-(CH₂)₃—CO  | (4R)—3-[1-(4-phenylbutyryl) pirrolidine-2-carbonyl] thiazolidin-4-al | 0.67 (EtOAc: CH₃OH = 9:1) | 1720, 1620, 1410, 1290, 1235, 1030, 740, 690 |
| 1 (p) | 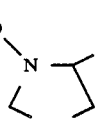 φ-(CH₂)₃—CO  | (4R)—3-[3-(4-phenylbutyryl) thiazolidine-4-carbonyl] thiazolidin-4-al | 0.33 (EtOAc: hexane = 2:1) | 1720, 1630, 1400, 1240, 1170, 1030, 740, 690 |
| 1 (q) | 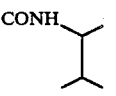 φ-(CH₂)₃—CONH  | (4R)—3-[2-(4-phenylbutyrylamino)-3-methylbutyryl]thiazolidin-4-al | 0.39 (hexane: EtOAc = 1:1) | (CHCl₃ Solution) 3450, 1730, 1640, 1490, 1410 |
| 1 (r) | φ-CH₂—N(CH₃)—CO—(CH₂)₂— | (4R)—3-[3-(N—benzyl-N—methyl carbamoyl)propionyl]thiazolidin-4-al | 0.25 (EtOAc) | 1720, 1630, 1390, 1240, 1160, 1030, 740, 690 |
| 1 (s) | φ-CH₂—N(φ)—CO—(CH₂)₂— | (4R)—3-[3-(N—benzyl-N—phenyl carbamoyl)propionyl]thiazolidin-4-al | 0.51 (EtOAc: hexane = 4:1) | 1720, 1630, 1590, 1485, 1390, 1260, 1070, 1010, 690 |
| 1 (t) | 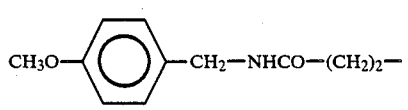 CH₃O—⟨⟩—CH₂—NHCO—(CH₂)₂— | (4R)—3-[3-[N—(4-methoxybenzyl) carbamoyl]propionyl]thiazolidin-4-al | 0.29 (EtOAc: CH₃OH = 95:5) | 3300, 2900, 1720, 1630, 1500, 1410, 1235 |

TABLE II-continued

| No. | R— | Name | TLC (Rf) | IR ($\nu cm^{-1}$) |
|---|---|---|---|---|
| 1 (u) | 4-Cl-C₆H₄-CH₂-NHCO-(CH₂)₂- | (4R)—3-[3-[N—(4-chlorobenzyl) carbamoyl]propionyl]thiazolidin-4-al | 0.24 (EtOAc: CH₃OH = 95:5) | 3300, 2900, 1720, 1620, 1530, 1480, 1400, 1080, 1000, 790, 740 |
| 1 (v) | φ-CH₂-NHCO-cyclopentyl | (4R)—3-[2-[N—benzylcarbamoyl) cyclopentanecarbonyl]thiazolidin-4-al | 0.35 (EtOAc: hexane = 3:1) | 3275, 1720, 1610, 1520, 1410, 1280, 1040, 685 |
| 1 (w) | φ-CH₂-N(CH₃)-CO-cyclopentyl | (4R)—3-[2-(N—benzyl-N—methyl carbamoyl)cyclopentanecarbonyl] thiazolidin-4-al | 0.56 (EtOAc) | 1720, 1620, 1390, 1290, 1030, 720, 680 |
| 1 (x) | naphthyl-CH₂-NHCO-(CH₂)₂- | (4R)—3-[3-[N—naphthyl)methyl carbamoyl]propionyl]thiazolidin-4-al | 0.18 (EtOAc) | (KBr) 3400~3200, 1720, 1630, 1530, 1410, 790 |
| 1 (y) | 4-Cl-C₆H₄-(CH₂)₂-CO-(CH₂)₂- | (4R)—3-[6-(4-chlorophenyl)-4-oxo hexanoyl]thiazolidin-4-al | 0.27 (EtOAc: hexane = 2:1) | 1715, 1640, 1485, 1405, 1365, 1240, 1090 |
| 1 (z) | 4-CH₃-C₆H₄-CH₂-N(φ)-CO-(CH₂)₂- | (4R)—3-[3-[N—(4-methylbenzyl)-N—phenylcarbamoyl]propionyl] thiazolidin-4-al | 0.55 (EtOAc) | (CHCl₃ solution) 1725, 1630, 1590, 1490, 1400 |
| 1 (aa) | 4-Cl-C₆H₄-CH₂-N(φ)-CO-(CH₂)₂- | (4R)—3-[3-[N—(4-chlorobenzyl)-N—phenylcarbamoyl]propionyl] thiazolidin-4-al | 0.16 (EtOAc: hexane = 1:1) | (CHCl₃ solution) 1725, 1640, 1590, 1485, 1395 |
| 1 (bb) | φ-CH₂-N(φ)-CO-(2R)-cyclopentyl | (4R)—3-[(2R)—2-(N—benzyl-N—phenyl carbamoyl)cyclopentanecarbonyl] thiazolidin-4-al | 0.34 (EtOAc: hexane = 1:1) | 1720, 1620, 1580, 1480, 1380, 1230, 1065, 1030, 765, 720, 690 |
| 1 (cc) | 4-Cl-C₆H₄-CH₂-N(CH₃)-CO-(CH₂)₂- | (4R)—3-[3-[N—(4-chlorobenzyl)-N—methylcarbamoyl]propionyl] thiazolidin-4-al | 0.20 (EtOAc) | 1725, 1635, 1485, 1400, 1240 |
| 1 (dd) | 4-CH₃-C₆H₄-CH₂-N(CH₃)-CO-(CH₂)₂- | (4R)—3-[3-[N—methyl-N—(4-methyl benzyl)carbamoyl]propionyl] thiazolidin-4-al | 0.19 (EtOAc) | 1625, 1630, 1400, 1240, 1040 |
| 1 (ee) | 2-naphthyl-CH₂-NHCO-(CH₂)₂- | (4R)—3-[3-[N—(2-naphthyl)methyl carbamoyl]propionyl]thiazolidin-4-al | 0.48 (EtOAc: CH₃OH = 9:1) | 2900, 1720, 1630, 1530, 1410, 1250, 810, 740 |
| 1 (ff) | 2-naphthyl-CH₂-N(CH₃)-CO-(CH₂)₂- | (4R)—3-[3-[N—methyl-N—(2-naphthyl) methylcarbamoyl]propionyl] thiazolidin-4-al | 0.23 (EtOAc) | 2900, 1720, 1650, 1620, 1410~1390, 1260, 1110, 810, 740 |

TABLE II-continued

| No. | R— | Name | TLC (Rf) | IR (νcm⁻¹) |
|---|---|---|---|---|
| 1 (gg) | 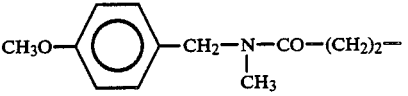 | (4R)—3-[3-[N—(4-methoxybenzyl)-N—methylcarbamoyl]propionyl]thiazolidin-4-al | 0.19 (EtOAc) | 1725, 1630, 1580, 1505, 1400, 1235, 1170, 1110, 1025 |
| 1 (hh) | 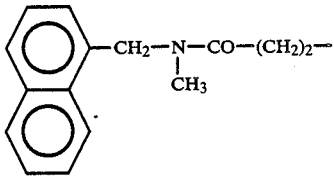 | (4R)—3-[3-[N—methyl-N—(1-naphthyl)methylcarbamoyl]propionyl]thiazolidin-4-al | 0.23 (EtOAc) | 1720, 1630, 1400, 1240, 1040 |
| 1 (ii) | φ-CH₂—NHCO—(CH₂)₂— | (4R)—3-[3-(N—benzylcarbamoyl)propinyl]thiazolidin-4-al | 0.47 (EtOAc: CH₃OH = 9:1) | 2900, 1720, 1640, 1330, 1410, 730, 690 |
| 1 (jj) | 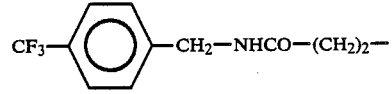 | (4R)—3-[3-[N—(4-trifluoromethylbenzyl)carbamoyl]propionyl]thiazolidin-4-al | 0.23 (EtOAc) | 3280, 1720, 1620, 1520, 1400, 1310, 1150, 1100, 1050, 1010, 800 |
| 1 (kk) | 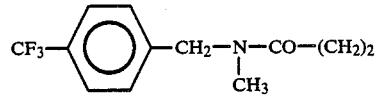 | (4R)—3-[3-[N—methyl-N—(4-trifluoromethylbenzyl)carbamoyl]propionyl]thiazolidin-4-al | 0.34 (EtOAc: CH₃OH = 19:1) | 2900, 1715, 1620, 1390, 1310, 1165, 1100, 1050, |
| 1 (ll) | 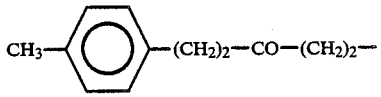 | (4R)—3-[4-oxo-6-(4-methylphenyl)hexanoyl]thiazolidin-4-al | 0.25 (EtOAc: hexane = 3:2) | (CHCl₃ solution) 1725, 1705, 1640, 1400 |
| 1 (mm) | 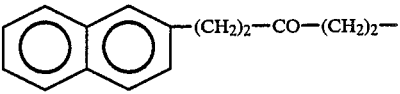 | (4R)—3-[6-(2-naphthyl)-4-oxohexanoyl]thiazolidin-4-al | 0.39 (EtOAc: hexane = 2:1) | 2900, 1715, 1630, 1400, 1350, 1230, 810, 740 |
| 1 (nn) | 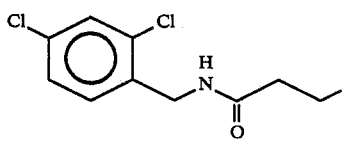 | (4R)—3-[3-[N—(2,4-dichlorobenzyl)carbamoyl]propionyl]thiazolidin-4-al | 0.48 (EtOAc: MeOH = 9:1) | (CHCl₃ solution) 1730, 1650, 1510, 1410, 1100 |
| 1 (oo) | 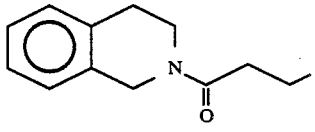 | (4R)—3-[4-(1,2,3,4-tetrahydro-isoquinolin-2-yl)-4-oxobutyryl]thiazolidin-4-al | 0.39 (EtOAc: MeOH = 9:1) | 2900, 1720, 1620, 1400, 1200, 740 |
| 1 (pp) | 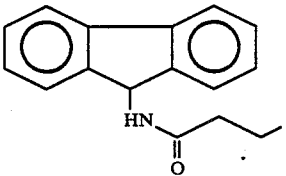 | (4R)—3-[3-[N—(9-fluorenyl)carbamoyl[propionyl]thiazolidin-4-al | 0.39 (EtOAc: hexane = 4:1) | (KBr tablet) 3250, 1720, 1620, 1520, 1400, 730 |

Formulation example

The following components were admixed in conventional method and punched out to obtain 100 tablets each containing 50 mg of active ingredient.

(4R)-3-[3-[N-(4-methylbenzyl) . . . 5 g, carbamoyl]-propionyl]thiazolidin-4-al

Cellulose calcium gluconate . . . 0.2 g, (disintegrating agent)

Magnesium stearate . . . 0.1 g, (lubricating agent)

Microcrystaline cellulose . . . 4.7 g

What is claimed is:

1. A novel thiazolidine derivative of general formula:

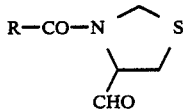

(I)

wherein R represents a group of general formula:

G-E-D-B-A- wherein A represents single bond, alkylene group of from 1 to 6 carbon atoms(s), alkenylene group of from 2 to 6 carbon atoms, a group of general formulae:

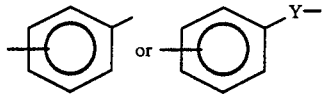

or saturated hydrocarbon ring of from 4 to 7 carbon atoms or mono heterocyclic ring containing 4 to 7 ring members including 1 or 2 hetero atom(s) selected from N, S and O, which may be partially or fully saturated or aromatic, Y represents alkylene group of from 1 to 4 carbon atoms(s) or alkenylene group of from 2 to 4 carbon atoms, B represents single bond or alkylene group of from 1 to 6 carbon atoms, D represents single bond, oxygen atom, carbonyl group or a group of general formulae:

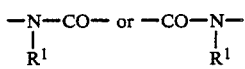

$R^1$ represents hydrogen atom, alkyl group of from 1 to 4 carbon atom(s), phenyl group or benzyl group, E represents single bond, alkylene group of from 1 to 8 carbon atom(s) or alkylene group of from 1 to 8 carbon atoms(s) substituted by phenyl group or benzyl group, G represents mono-, bi-, or tri-carbocyclic ring(s) containing not more than 15 carbon atoms which may be partially or fully saturated or aromatic or G represents mono-, bi-, or tri-heterocyclic ring(s) containing not more than 15 ring members including carbon and one or two hetero atom(s) selected from O, N and S which may be partially or fully saturated or aromatic, wherein said carbocyclic or heterocyclic ring(s) represented by G are unsubstituted or substituted by from 1 to 3 of alkyl group of from 1 to 6 carbon atom(s), alkoxy group of from 1 to 6 carbon atom(s), halogen atom, trifluoromethyl group or nitro group, with the proviso that A nd B do not represent single bonds at the same time.

2. A compound according to claim 1, wherein G is benzene or naphthalene ring unsubstituted or substituted by substituent(s).

3. A compound according to claim 2, wherein A is alkylene group of from 1 to 6 carbon atom(s) or saturated hydrocarbon ring of from 4 to 7 carbon atoms, and D is single bond.

4. A compound according to claim 1 or 3, which is selected from the group consisting of:

(4R)-3-(4-phenylbutyryl)thiazolidin-4-al,
(4R)-3-(10-phenyldecanoyl)thiazolidin-4-al,
(4R)-3-(2-isopropyl-7-phenylheptanoyl)thiazolidin-4-al,
(4R)-3-[2-(4-phenylbutyl)cyclohexanecarbonyl]-thiazolidin-4-al,
(4R)-3-[7-(4-chlorophenyl)-2-isopropylheptanoyl]-thiazolidin-4-al
and
(4R)-3-[3-(4-butylphenyl)propionyl]thiazolidin-4-al.

5. A compound according to claim 2, wherein A is a group of the general formula:

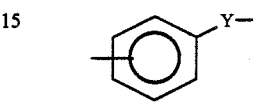

(wherein Y is the same meaning as defined in claim 1.), and D is single bond or oxygen atom.

6. A compound according to claim 1 or 5, which is selected from the group consisting of:

(4R)-3-[4-(5-phenylpentyl)cinnamoyl]thiazolidin-4-al
and
(4R)-3-[4-(4-phenylbutoxy)cinnamoyl]thiazolidin-4-al.

7. A compound according to claim 2, wherein A is alkylene group of from 1 to 6 carbon atom(s), and D is oxygen atom.

8. A compound according to claim 1 or 7, which is (4R)-3-(4-benzyloxybutyryl)thiazolidin-4-al.

9. A compound according to claim 2, wherein A is alkylene group or saturated hydrocarbon ring of from 4 to 7 carbon atoms, and D is carbonyl group.

10. A compound according to claim 1 or 9, which is selected from the group consisting of:

(4R)-3-(4-oxo-4-phenylbutyryl)thiazolidin-4-al,
(4R)-3-(4-oxo-7-phenylheptanoyl)thiazolidin-4-al,
(4R)-3-[(2R)-2-(3-phenylpropionyl)cyclopentanecarbonyl]thiazolidin-4-al,
(4R)-3-[6-(1-naphthyl)-4-oxohexanoyl]thiazolidin-4-al,
(4R)-3-[6-(4-chlorophenyl)-4-oxohexanoyl]thiazolidin-4-al,
(4R)-3-[4-oxo-6-(4-methylphenyl)hexanoyl]thiazolidin-4-al,
(4R)-3-[6-(2-naphthyl)-4-oxohexanoyl]thiazolidin-4-al,
and
(4R)-3-[4-(1,2,3,4-tetrahydroquinolin-2-yl)-4-oxobutyryl]thiazolidin-4-al.

11. A compound according to claim 2, wherein A is pyrrolidine ring, piperidine ring or thiazolidine ring, and D is carbonyl group.

12. A compound according to claim 1 or 11, which is selected from the group consisting of:

(4R)-3-[1-(3-phenylpropionyl)piperidine-2-carbonyl]-thiazolidin-4-al,
(4R)-3-[1-(4-phenylbutyryl)pyrrolidine-2-carbonyl]-thiazolidin-4-al
and
(4R)-3-[3-(4-phenylbutyryl)thiazolidine-4-carbonyl]-thiazolidin-4-al.

13. A compound according to claim 2, wherein A is alkylene group of from 1 to 6 carbon atom(s), and D is a group of the general formula:

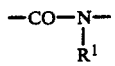

(wherein R¹ is the same meaning as defined in claim 1.).

14. A compound according to claim 1 or 13, which is: (4R)-3-[2-(4-phenylbutyrylamino)-3-methylbutyryl]-thiazolidin-4-al.

15. A compound according to claim 2, wherein A is alkylene group of from 1 to 6 carbon atom(s), and D is a group of the general formula:

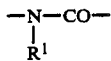

(wherein R¹ is the same meaning as defined in claim 1.).

16. A compound according to claim 1 or 15, which is selected from the group consisting of:
(4R)-3-[3-[N-(4-methylbenzyl)carbamoyl]propionyl]-thiazolidin-4-al,
(4R)-3-[3-(N-benzyl-N-methylcarbamoyl)propionyl]-thiazolidin-4-al,
(4R)-3-[3-(N-benzyl-N-phenylcarbamoyl)propionyl]-thiazolidin-4-al,
(4R)-3-[3-[N-(4-methoxybenzyl)carbamoyl]propionyl]thiazolidin-4-al,
(4R)-3-[3-[N-(4-chlorobenzyl)carbamoyl]propionyl]-thiazolidin-4-al,
(4R)-3-[2-[N-benzylcarbamoyl)cyclopentanecarbonyl]thiazolidin-4-al,
(4R)-3-[2-(N-benzyl-N-pentylcarbamoyl)cyclopentanecarbonyl]thiazolidin-4-al,
(4R)-3-[3-[N-(1-naphthyl)methylcarbamoyl]propionyl]thiazolidin-4-al,
(4R)-3-[3-[N-(4-methylbenzyl)-N-phenylcarbamoyl]-propionyl]thiazolidin-4-al,
(4R)-3-[3-[N-(4-chlorobenzyl)-N-phenylcarbamoyl]-propionyl]thiazolidin-4-al,
(4R)-3-[(2R)-2-(N-benzyl-N-phenylcarbamoyl)cyclopentanecarbonyl]thiazolidin-4-al,
(4R)-3-[3-[N-(4-chlorobenzyl)-N-methylcarbamoyl]-propionyl]thiazolidin-4-al,
(4R)-3-[3-[N-methyl-N-(4-methylbenzyl)carbamoyl]-propionyl]thiazolidin-4-al,
(4R)-3-[3-[N-(2-naphthyl)methylcarbamoyl]propionyl]thiazolidin-4-al,
(4R)-3-[3-[N-methyl-N-(2-naphthyl)methylcarbamoyl]propionyl]thiazolidin-4-al,
(4R)-3-[3-[N-(4-methoxybenzyl)-N-methylcarbamoyl]propionyl]thiazolidin-4-al,
(4R)-3-[3-[N-methyl-N-(1-naphthyl)methylcarbamoyl]propionyl]thiazolidin-4-al,
(4R)-3-[3-(N-benzylcarbamoyl)propionyl]thiazolidin-4-al,
(4R)-3-[3-[N-(4-trifluoromethylbenzyl)carbamoyl]-propionyl]thiazolidin-4-al,
(4R)-3-[3-(N-benzylcarbamoyl)propionyl]thiazolidin-4-al,
(4R)-3-[3-[N-(2,4-dichlorobenzyl)carbamoyl]propionyl]thiazolidin-4-al
and
(4R)-3-[3-[N-(9-fluorenyl)carbamoyl]propionyl]-thiazolidin-4-al.

17. A pharmaceutical composition for treating amnesia which comprises an effective amount of thiazolidine derivative of the general formula (I) and pharmaceutically acceptable carrier and/or coating.

18. The method for treating amnesia which comprises administering a therapeutically effective amount of thiazolidine derivative of the general formula (I).

* * * * *